(12) United States Patent
Ruth et al.

(10) Patent No.: US 10,060,865 B2
(45) Date of Patent: Aug. 28, 2018

(54) MEASUREMENT OF CRITICAL DIMENSIONS OF NANOSTRUCTURES USING X-RAY GRAZING INCIDENCE IN-PLANE DIFFRACTION

(71) Applicant: Lyncean Technologies, Inc., Fremont, CA (US)

(72) Inventors: Ronald D. Ruth, Stanford, CA (US); Roderick J. Loewen, Redwood City, CA (US); Martin A. Gifford, Palo Alto, CA (US)

(73) Assignee: Lyncean Technologies, Inc., Fremont, CA (US)

( * ) Notice: Subject to any disclaimer, the term of this patent is extended or adjusted under 35 U.S.C. 154(b) by 87 days.

(21) Appl. No.: 15/065,637

(22) Filed: Mar. 9, 2016

(65) Prior Publication Data

US 2016/0266056 A1    Sep. 15, 2016

Related U.S. Application Data

(60) Provisional application No. 62/131,082, filed on Mar. 10, 2015.

(51) Int. Cl.
*G01N 23/207* (2006.01)
*G01B 15/00* (2006.01)

(52) U.S. Cl.
CPC .......... *G01N 23/207* (2013.01); *G01B 15/00* (2013.01); *G01B 2210/56* (2013.01); *G01N 2223/6116* (2013.01)

(58) Field of Classification Search
CPC .. G01B 15/00; G01B 2210/56; G01N 23/207; G01N 2223/6116
See application file for complete search history.

(56) References Cited

U.S. PATENT DOCUMENTS

| | | |
|---|---|---|
| 6,556,652 B1 | 4/2003 | Mazor et al. |
| 7,035,373 B2 | 4/2006 | Omote |
| 7,110,491 B2 | 9/2006 | Mazor et al. |
| 7,483,513 B2 | 1/2009 | Mazor et al. |
| 7,920,676 B2 | 4/2011 | Yun et al. |
| 8,908,830 B2 | 12/2014 | Omote et al. |
| 8,934,607 B2 | 1/2015 | Ishibashi |
| 2008/0159479 A1 | 7/2008 | Huang et al. |
| 2011/0255668 A1 | 10/2011 | Hoghoj et al. |

(Continued)

FOREIGN PATENT DOCUMENTS

WO    2012056413    5/2012

OTHER PUBLICATIONS

Sunday et al. Current Status of CDSAXS: Is it Fab-Ready?—National Institute of Standards and Technology. Apr. 14, 2015.

(Continued)

*Primary Examiner* — Mark R Gaworecki
(74) *Attorney, Agent, or Firm* — Van Pelt, Yi & James LLP

(57) ABSTRACT

The manufactured structure is illuminated with an x-ray beam. The manufactured structure is positioned at a selected grazing angle and a selected rotation angle with respect to the x-ray beam. The selected rotation angle has been selected to enhance in-plane diffraction of reflections of the x-ray beam by the manufactured structure. A grazing in-plane diffraction beam produced by interference with the periodic feature is detected. A property of the grazing in-plane diffraction beam is determined by the critical dimension.

54 Claims, 17 Drawing Sheets

(56) References Cited

U.S. PATENT DOCUMENTS

2013/0314710 A1  11/2013  Levy et al.
2015/0117610 A1  4/2015  Veldman et al.

OTHER PUBLICATIONS

Ho et al. A Laboratory Scale Critical-Dimension Small-Angle X-ray Scattering Instrument. ReseachGate. Sep. 2007.

Tanner etal. Grazing Incidence In-Plane X-Ray Diffraction in the Laboratory. Copyright (c)JCPDS—International Centre for Diffraction Data 2004, Advances in X-ray Analysis, vol. 47.

Mark Lapedus. Gaps in Metrology Could Impact Yield. Apr. 17, 2014: http://semiengineering.com/gaps-in-metrology-could-impact-yield/.

gisaxs.com. GISAXS Community Website. Last modified on Nov. 17, 2014.

Wu et al. Dimensional Metrology for Nanoscale Patterns. NIST-led development project for X-ray CD-SAXS evaluation (2008); http://www.nist.gov/mml/msed/functional_polymer/dimensional-metrology.cfm.

Bunday et al. Gaps Analysis for CD Metrology Beyond the 22nm Node. Proc. SPIE Conference 8681, Metrology, Inspection, and Process Control for Microlithography XXVII, San Jose Convention Center & San Jose Marriott, Feb. 24-28, 2013.

V. G. Kohn. On the Theory of Reflectivity by an X-Ray Multilayer Mirror. phys. stat. sol (b) 187, 61 (1995).

Stepanov et al. Dynamical x-ray diffraction of multilayers and superlattices: Recursion matrix extension to grazing angles. Phys. Rev. B, v.57, No. 8, p. 4829-4841, Feb. 15, 1998.

Sunday et al. Determining the shape and periodicity of nanostructures using small angle X-ray scattering. Journal of Applied Crystallography. 48, 1355-1363.2015.

Settens et al. CD-SAXS measurements of FinFet and 3D memory structures. SPIE Advanced Lithography. Feb. 26, 2013.

Zhou et al. Weighted-superposition approximation for x-ray and neutron reflectance. Physical Review E, vol. 49, No. 6. Jun. 1994.

Stepanov et al. A matrix approach to x-ray grazing-incidence diffraction in multilayers. Zeitschrift fuer Physik B, v.96, No. 3, p. 341-347, (1995).

L. G. Parratt. Surface Studies of Solids by Total Reflection of X-Rays. Phys. Rev. 95, 359. Published Jul. 15, 1954.

Hu et al. Small angle x-ray scattering metrology for sidewall angle and cross section of nanometer scale line gratings, Journal of Applied Physics, 96, 1983-1987 (2004), DOI:http://dx.doi.org/10.1063/1.1773376.

Als-Nielsen et al. Elements of Modem X-ray Physics. 2nd Edition. Apr. 2011.

Yu et al., "Parratt-based and model-independent X-ray reflectivity filling procedure for nanoscale thin film characterization" In: Journal of Nanoscience and Nanotechnology, vol. 11, No. 5, pp. 4624-4628(5) [online]; May 1, 2011; [retrieved on May 10, 2016]. Retrieved from the internet <URL: http://www.ingentaconnect.com/content/asp/jnn/2011/00000011/00000005/art00149?crawler=true> <DOI: http://dx.doi.org/10.1166/jnn.2011.3689>.

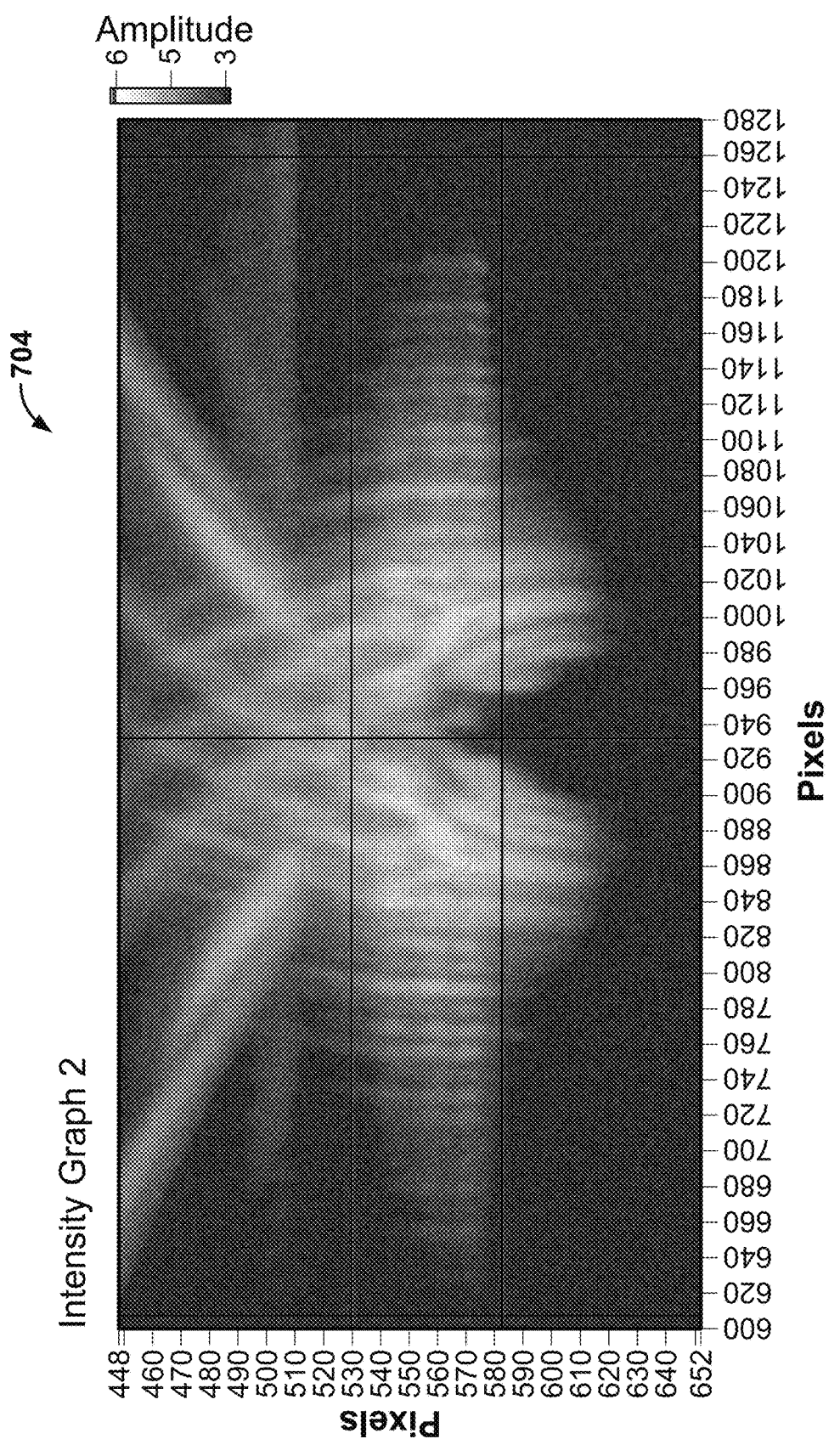

MEASUREMENT OF CRITICAL DIMENSIONS OF NANOSTRUCTURES USING X-RAY GRAZING INCIDENCE IN-PLANE DIFFRACTION

CROSS REFERENCE TO OTHER APPLICATIONS

This application claims priority to U.S. Provisional Patent Application No. 62/131,082 entitled MEASUREMENT OF CRITICAL DIMENSIONS OF NANOSTRUCTURES USING X-RAY GRAZING INCIDENCE IN-PLANE DIFFRACTION filed Mar. 10, 2015 which is incorporated herein by reference for all purposes.

BACKGROUND OF THE INVENTION

Semiconductor devices and nanometer scale systems are rapidly being reduced in size. During manufacturing and testing steps, critical dimensions of these manufactured devices need to be measured and verified to ensure device performance. Conventionally, light at UV wavelengths has been utilized in Optical Critical Dimension (OCD) technology to verify device critical dimensions. However, at dimensions below 100 nm, utilizing these conventional techniques is increasingly more challenging as dimensions become smaller than the wavelength of UV light. One potential alternative beam source is x-ray that has wavelengths better matched to smaller features. However, typical constructions in wafer fabrication have features which are present only on or near the surface of a substrate. Thus, the total volume that participates in scattering x-rays within a cross-sectional exposure is limited.

BRIEF DESCRIPTION OF THE DRAWINGS

Various embodiments of the invention are disclosed in the following detailed description and the accompanying drawings.

FIG. 7B shows intensity pattern 704 that depicts an aggregation of several intensity patterns at different in-plane rotation angles in log scale.

DETAILED DESCRIPTION

Figure 1A:
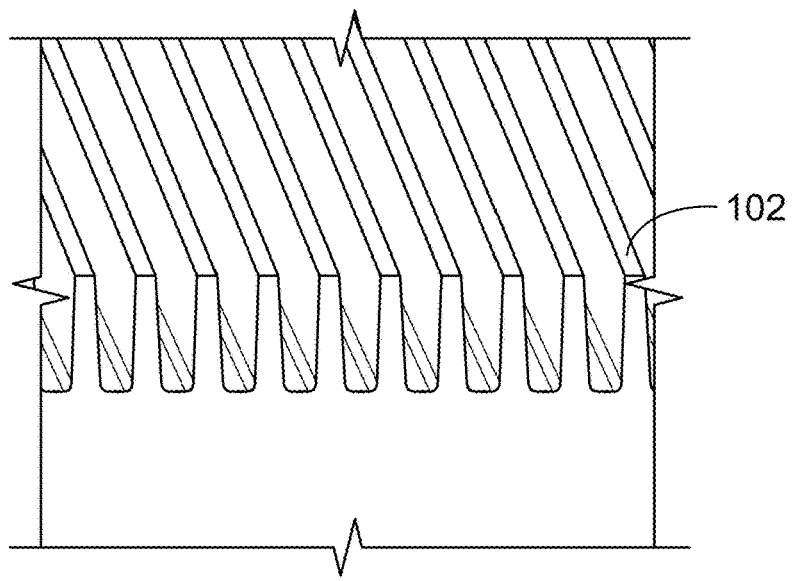
FIGS. 1A, 1B, and 1C are diagrams illustrating an example of a sample to be characterized.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Analyzing a manufactured structure having a periodic feature characterized by a critical dimension is disclosed. The structure is illuminated with an x-ray beam. In some embodiments, rather than requiring parallel collimated x-rays, an x-ray beam with a larger divergence may be utilized to allow faster and more efficient measurements. The x-ray beam is illuminated at a grazing angle with respect to the manufactured structure and produces a grazing in-plane diffraction beam. For example, when the x-ray beam hits a surface of the manufactured structure, at least a portion of the x-ray beam is reflected from the surface and hits a detector. The x-ray beam may be oriented to illuminate the features on the manufactured structure both along the predominate feature direction and at an angle to this direction in order to produce multiple opportunities for such feature to reflect the x-ray beam. These periodic features my cause multiple reflections between them. The resulting grazing in-plane diffraction beams constructively and destructively interfere with each other to produce a diffraction pattern. The grazing in-plane diffraction beam produced by interference with the periodic structure is detected. A property of the grazing in-plane diffraction beam is determined by the critical dimension and the critical dimension is characterized based on the property of the grazing in-plane diffraction beam. For example, based on the detected interference pattern, a measurement and/or periodicity is determined and/or verified against an ideal reference.

One potential method to utilize x-rays is to use near normal incidence of x-rays to detect grating-like diffraction from semiconductor nanostructures. Using Critical Dimension Small-Angle X-ray Scattering (CD-SAXS), x-ray beams that pass through a sample, normal to the surface, (e.g., transmission mode) are detected and analyzed. The variation in thickness of the structure alters the phase of the transmitted x-rays and these phase differences create the diffraction pattern. However, transmission mode techniques require extremely intense x-ray beams that are also very bright (e.g., with both small spot size and small angular divergence), due to the extremely small cross section for scattering from the thin layer of material. Because the scattering intensity is proportional to the phase shift of the x-rays as they pass through the variations on the sample device, as feature sizes decrease in height with newer semiconductor and nano-manufacturing technologies, the cross sectional variations causing scattering decreases proportionally. Additionally many of the CD-SAXS studies have used x-rays from synchrotron sources to characterize the method and these large synchrotrons cannot be realistically utilized in a semiconductor fabrication plant for process control. Laboratory sources are too weak to exploit these methods for typical process control applications due to the impractically long measurement times. Additionally CD-SAXS is a transmission method where the x-rays have to transverse the substrate, in most cases a Silicon wafer with several hundred micrometers thickness. This requires the use of higher energy x-rays that have weak interaction with the structure to be measured and additionally get strongly attenuated passing through the substrate. Thus the effectiveness of transmission mode techniques is limited due to the small cross sectional variations for scattering through a single thin layer of material.

Another potential method to utilize x-rays is to use a reflection of an x-ray beam (e.g., reflection mode) instead of using transmission mode x-ray beams at near normal incidence to the sample. By using a beam at a grazing incidence angle, to allow a beam grazing the structure of the sample to be reflected, the scattering signal strength can be increased substantially. By illuminating the sample at a small angle, the beam travels for a longer distance within depths of features of the sample. Thus by using a grazing incidence angle to illuminate the sample, the geometric projection of the nanostructures leads to a larger cross-section for scattering. However, the required footprint of the beam and sample may be large in the beam direction to take advantage of the increased cross section. Additionally, the issue of absorption within the substrate gets resolved since the x-rays reflect off the substrate surface.

These reflection mode techniques such as grazing-incidence small-angle scattering (GISAXS) or CD-GISAXS utilize focused and collimated x-ray beams pointed towards a sample at grazing-incidence angle and the scattering from the sample is recorded with a detector. Typically the brightness requirements for the x-ray source for these techniques are also extremely high due to the requirement of both small x-ray spot size and small angular divergence. The beam interaction of interest is Fraunhoffer diffraction from the sample's periodic structure that gives rise to scattering features. However, by design, techniques such as GISAXS align the structure so as to illuminate the features along their predominate direction. The angle of incidence relative to this direction is nearly zero. This can be contrasted with respect to Critical Dimension Grazing Incidence In-Plane Diffraction, where the sample is rotated in-plane to enhance higher order reflections.

In some embodiments, Critical Dimension Grazing Incidence In-Plane Diffraction (CD-GIID) is utilized to characterize a critical dimension of a manufactured device sample. Not only does utilizing CD-GIID utilize an x-ray beam oriented at a grazing angle with respect to the sample to cause a reflection of the beam on the sample surface, the sample is rotated in-plane to cause higher order reflections from the periodic features of the sample rather than minimizing them. At certain angles, these higher order reflections have phase shifts between the reflected beams that constructively or destructively interfere, depending upon the angle, to create higher order diffraction patterns detected on a two-dimensional detector that can be analyzed to determine characteristics of the critical features of the sample. The beam illumination of the sample is geometrically constrained for near specular reflection in the vertical out of plane direction, which requires both a combination of illuminated angles and sample positioning. By varying the angle of in-plane incidence, a modulated intensity map of scattered x-rays is collected on the detector. In some embodiments, the resulting pattern can be parametrically fit to physical models of the periodic structure. CD-GIID has the added benefit of being sensitive to features in three-dimensions by taking data in a set of variable orientations and collecting two-dimensional data on area detectors such as scintillator-coupled CCDs.

Both CD-SAXS and CD-GISAXS rely mainly on the analysis of Fraunhofer (grating) diffraction. This diffraction arises from coherent addition of scattering sites which are orthogonal to the incident plane. In contrast, CD-GIID utilizes mainly Laue-Bragg diffraction. Laue-Bragg diffraction is a three-dimensional generalization of the coherent addition of waves in which the incident wave can be at any arbitrary angle to periodic scattering sites, which are often described as Bragg reflectance planes. The scattering sites may be individual atoms, such as in crystallography, or interfaces, such as in multilayer coatings.

Fundamentally, in low absorption materials, the superposition or coherence effects of photon scattering are enhanced by increasing the amount of material in the photon's path. In particular, multiple interfaces along photon paths lead to oscillations of reflectivity due to either variations in photon wavelength or angle of incidence, whereby the oscillation peaks can be used to infer layer thicknesses, composition, and other properties of the lattice. Bragg reflective techniques, such as CD-GIID, naturally separate the transmitted beam path from that of the reflected beam used for measurement and analysis, improving the ability to detect weak signals from the background. The coherent scattering amplitude arising throughout the electron density of the materials may be separated from the transmitted, non-scattered beam and leads to enhanced signal to noise.

Additionally, typical CD-SAXS and CD-GISAXS techniques require the use of a substantially parallel intense x-ray beam source because any spread of angles in the beam is inherited for every diffraction order. Thus, the clear separation of order is 'filled in' by the angular spread and for sufficiently large angular spread, the orders are not visible at all. In order to achieve the intense parallel beams, the x-ray beams are collimated, and the beams have to be extremely intense to compensate for intensity lost during collimation. However, with CD-GIID, the surface structure effectively acts as an angular filter that has very high reflectivity at only particular angles. Thus, it is possible to directly utilize an x-ray beam source with a divergent spread of angles without requiring collimation because only particular trajectories within the beam that are at particular angles will be highly reflected for detection. Without the need for collimation, it is possible to utilize a more intense x-ray beam which has not been weakened, often by the use of apertures, for collimation. Also by using a beam source with a spread of multiple angles, data for multiple beam angles may be collected simultaneously, which effectively reduces the data collection time. Additionally, multiple measurement scans may be performed by changing the angle of the sample with respect to the beam for each measurement instance and the results of multiple measurements (e.g., multiple diffraction patterns detected for different measurements) may be combined together to create a combined diffraction pattern with many orders of reflections in the plane of an area of the detector. This combined diffraction pattern may be analyzed to characterize the critical dimensions of the sample. In various embodiments, analysis of x-ray scattering can be extended to 3D by modeling periodic unit cells along preferred planes of orientation.

Figure 1B:
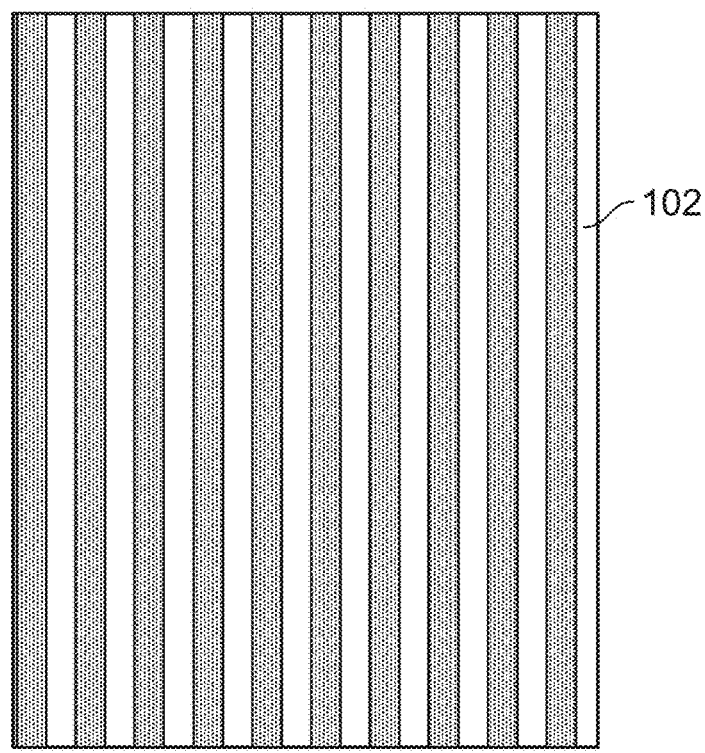
Figure 1C:
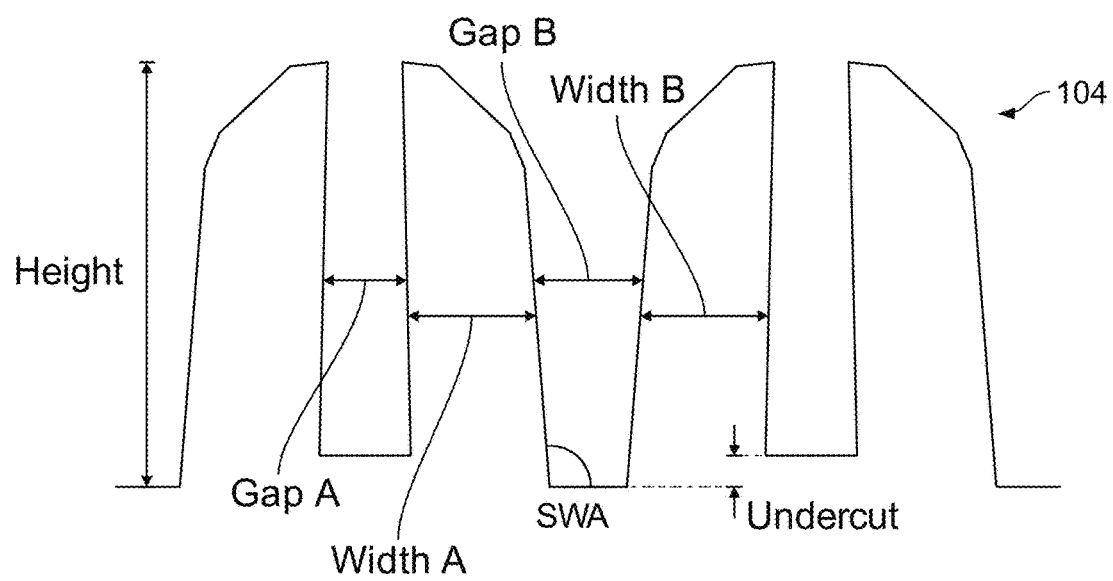

FIGS. 1A, 1B and 1C are diagrams illustrating an example of a sample to be characterized. Manufactured device sample 102 is shown in magnified view in FIGS. 1A and 1B. FIG. 1A shows a microscope magnified profile view of rows of raised "Fin" features of device sample 102. FIG. 1B shows a microscope magnified top view of device sample 102. These rows of raised "Fin" features of device sample 102 are example periodic features, such as might be constructed during the fabrication of FinFET transistors. In various embodiments, features of a manufactured structure are periodic if the features are repeated for at least two periods. However, periodic features are typically repeated for at least ten periods and possibly may be repeated for thousands of periods. The periodic features of device sample 102 are characterized by a critical dimension. The critical dimension may correspond to a dimension measurement of a feature geometry of interest that is monitored to maintain device performance and consistency. For example, FIG. 1C illustrates double pattern Fin structure 104 in which the fundamental in-plane periodic structure consists of two gaps and two linewidths. Furthermore, two dimensional scattering measurements can be fit to modeled parameters in out of plane features (e.g., overall height of Fins) or to variations of in-plane structures (e.g. sidewall angle (SWA)).

Figure 2:
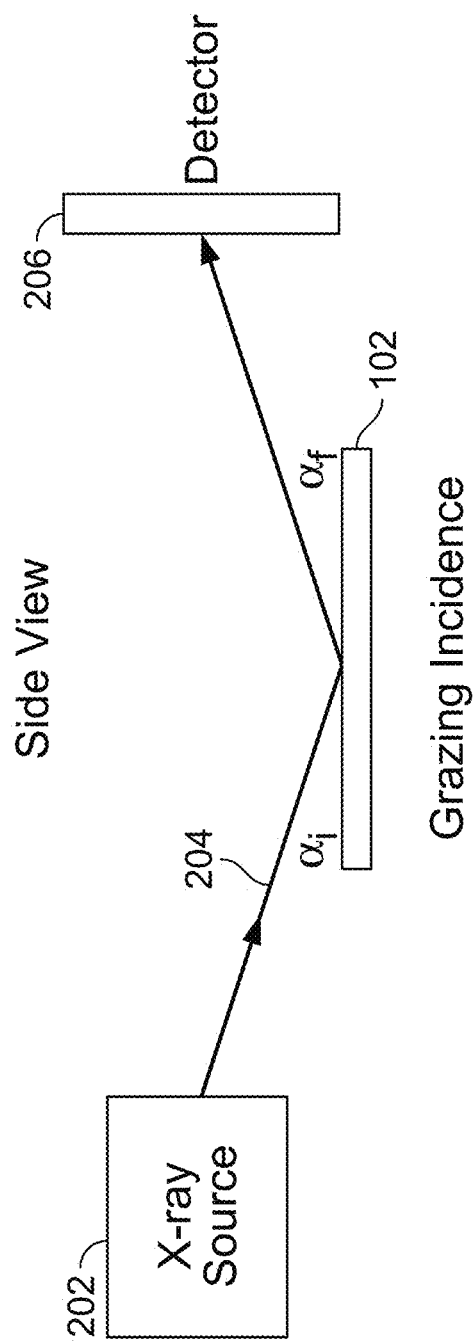
FIG. 2 is a diagram illustrating a side view of an example showing a reflective geometry of an x-ray beam utilized to analyze a manufactured structure.

FIG. 2 is a diagram illustrating a side view of an example showing a reflective geometry of an x-ray beam utilized to analyze a manufactured structure. X-ray source 202 generates x-ray beam 204 that illuminates device sample 102. X-ray beam 204 hits device sample 102 at a grazing incidence angle $\alpha_i$ and reflects off device sample 102 at an angle $\alpha_f$ (which may be equal to $\alpha_i$) with respect to the surface of device sample 102 that reflects x-ray beam 204. In various embodiments, the term "grazing incidence" is utilized to distinguish geometries in which an x-ray beam does not penetrate a sample but is reflected with high efficiency at or near the surface of the sample. The reflected x-ray beam is detected at detector 206. Detector 206 includes a two-dimensional detector area where reflected and diffracted x-rays are detected in the plane of the two-dimensional area. The reflection mode example shown in FIG. 2 can be contrasted with transmission mode (e.g., CD-SAXS) techniques that detect x-rays that pass through the sample rather than reflected x-rays.

Figure 3A:
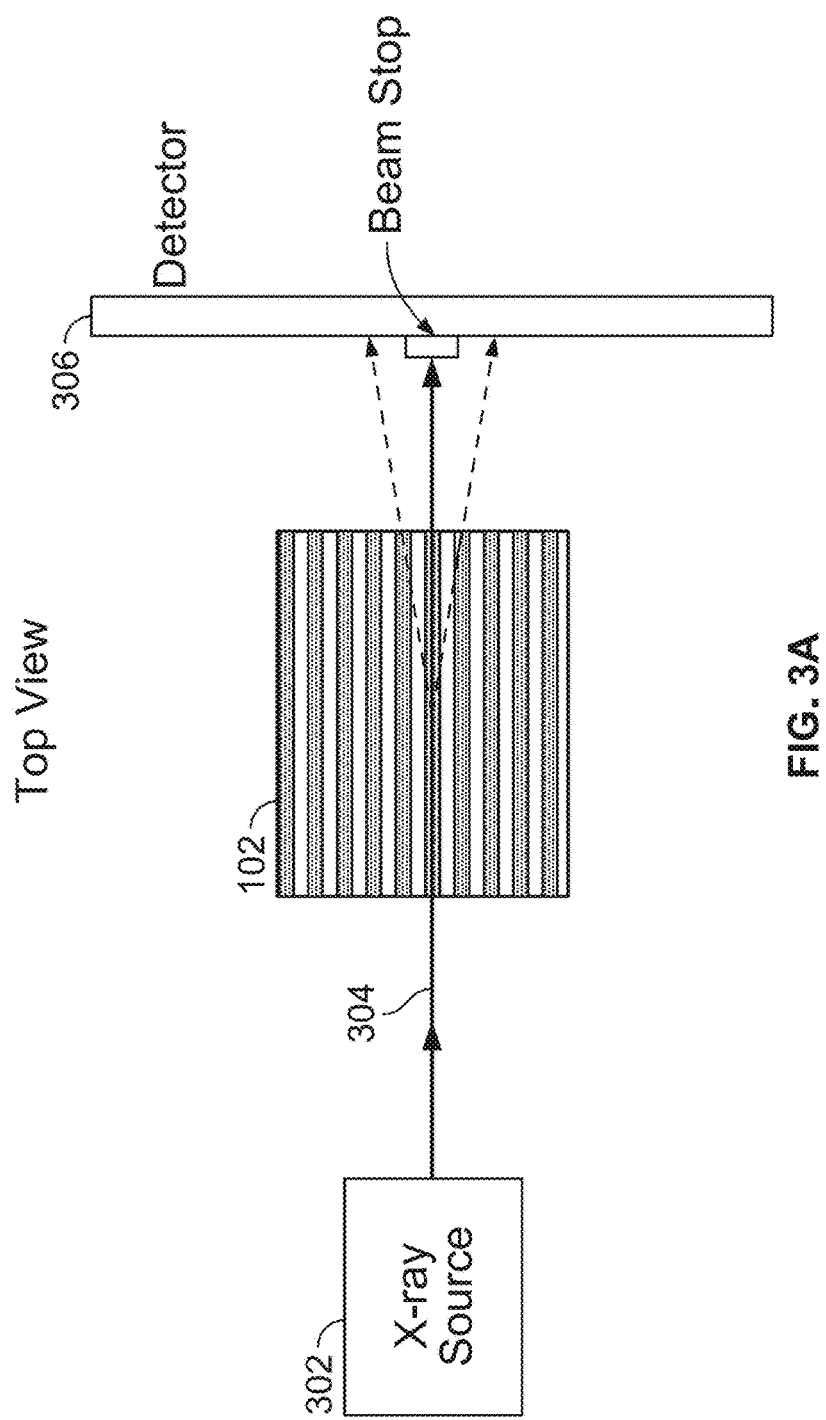
FIG. 3A is a diagram illustrating a top view and FIG. 3B is a diagram illustrating a profile view of an example showing a collimated x-ray beam being utilized to capture GISAXS data in analyzing a manufactured structure.
Figure 3B:
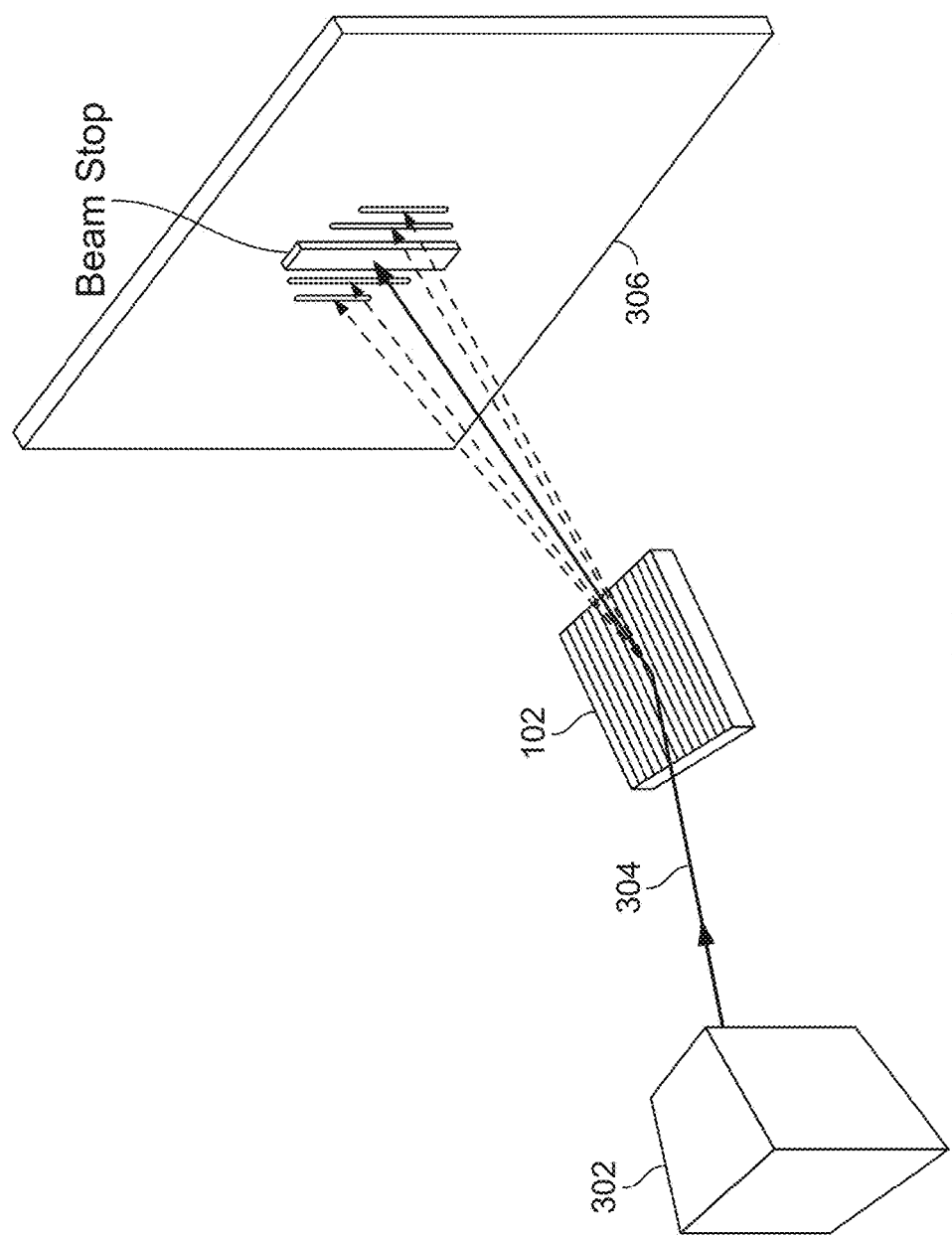

FIG. 3A is a diagram illustrating a top view and FIG. 3B is a diagram illustrating a profile view of an example showing a collimated x-ray beam being utilized to capture GISAXS data in analyzing a manufactured structure. X-ray source 302 generates x-ray beam 304 that illuminates device sample 102. X-ray beam 304 hits device sample 102 at an angle and reflects off device sample 102. By using a beam at a grazing incidence to allow a beam grazing the structure of the sample to be reflected, scattering signal strength can be increased. For example, by illuminating the sample at a small angle, the beam travels further within depths of features of the sample.

GISAXS requires fine alignment of sample features along its beam direction. Sample 102 has been oriented to align the rows of its raised "fin" features with the beam in order to maximize the distance traveled by the beam within the depths between the rows. Because the beam interaction of interest is mainly low order reflections that interact with the sample's structure that give rise to scattering, sample 102 has been oriented by design to minimize asymmetries in the measurement due to the interference of features along the in-plane direction. The reflected beam is attenuated by the beam stop and the beam stop prevents the detector from saturating when detecting scattering. The diffraction pattern resulting from scattering of the low order reflected beams is captured by detector 306. The diffraction pattern resulting from this scattering can be detected close to the center of the directly reflected central beam attenuated by the beam stop. X-ray beam 304 has been collimated and is configured to be extremely bright due to the requirements of both small x-ray spot size and small angular divergence required to produce a strong diffraction pattern that is well defined and not obscured by large angle variations which can be inherited at each order.

Figure 4A:
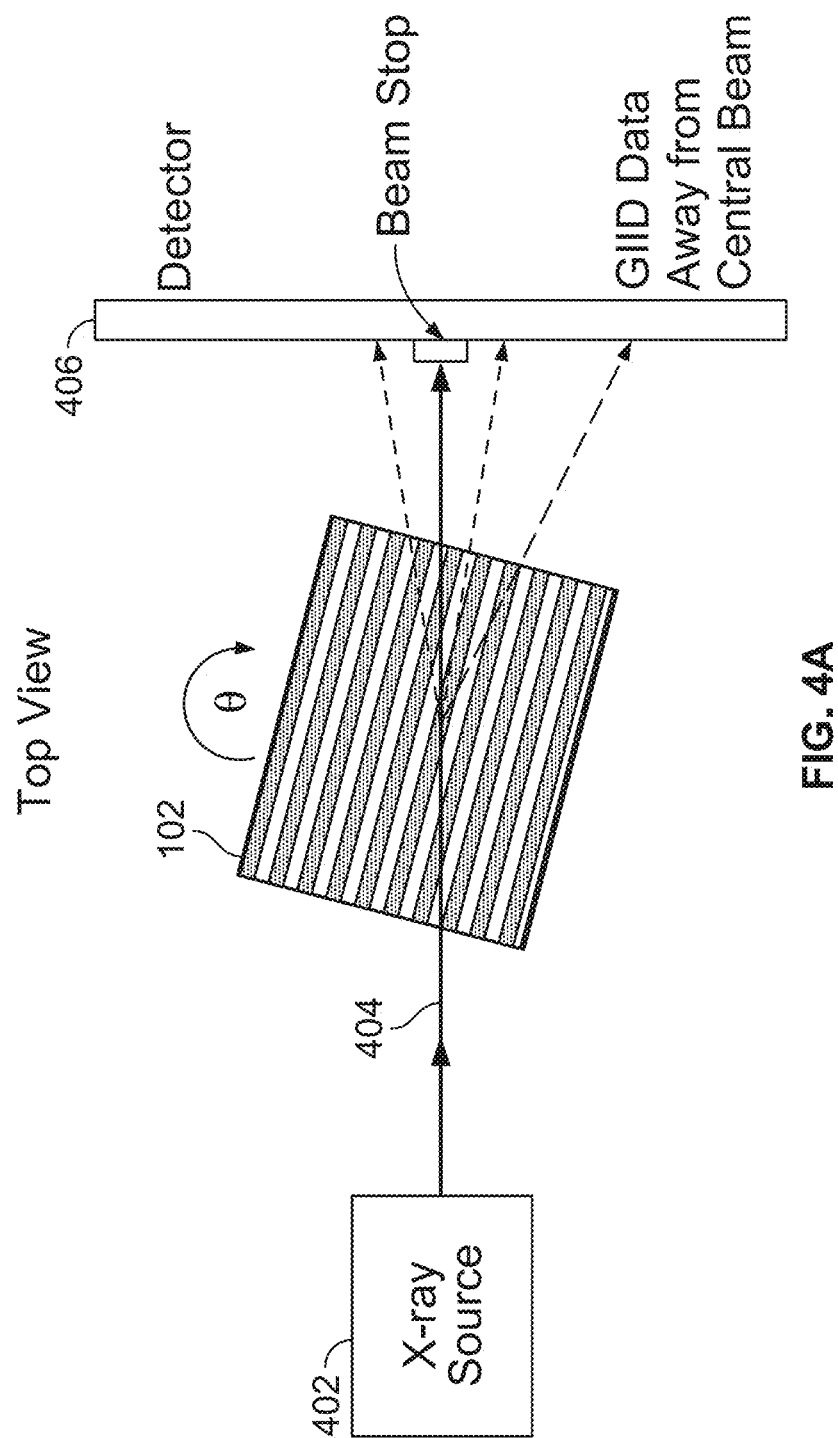
FIG. 4A is a diagram illustrating a top view of an example of a showing of a collimated x-ray beam being utilized to capture CD-GIID data in analyzing a manufactured structure.

FIG. 4A is a diagram illustrating a top view of an example of a showing of a collimated x-ray beam being utilized to capture CD-GIID data in analyzing a manufactured structure.

X-ray source 402 generates x-ray beam 404 that illuminates device sample 102. X-ray beam 404 hits device sample 102 at a grazing angle (e.g., shown as $\alpha_i$ in FIG. 2) and reflects off device sample 102 at the nearly the same angle (in this instance) with respect to the surface of device sample 102 that reflects x-ray beam 404. However, unlike the GISAXS example of FIGS. 3A and 3B, sample 102 has been further rotated in-plane by angle θ with respect to x-ray beam 404. At least some of the scattered beam is specularly reflected, which means for a θ rotation of the sample with respect to the beam, the beam is reflected 2θ away from the transmitted beam. In various embodiments, non-specular beam reflections at angles other than 2θ are also detected and analyzed. In some embodiments, the rotation of θ is in the plane normal to the plane of the grazing angle (e.g., plane of angle α in FIG. 2). By rotating the sample in the direction θ with respect to the beam, the beam is no longer parallel to the rows of the sample as configured in the example of FIGS. 3A and 3B. Unlike GISAXS, in order to generate CD-GIID data, sample 102 and x-ray beam 404 have been aligned to cause higher order Bragg/Laue reflections between the periodic features of sample 102.

The reflected x-ray beam is detected at detector 406. Detector 406 includes a two-dimensional detector area where reflected and diffracted x-rays are detected in the plane of the two-dimensional area. An example of detector 406 is scintillator-coupled CCDs. The CD-GIID data may be captured on detector 406 away from the central directly reflected beam and the diffraction from first order reflection. X-ray source 402 produces a beam that is collimated to produce a substantially parallel x-ray beam.

Examples of x-ray source 402 include conventional laboratory sources such as a microfocus, rotating anode, or liquid metal jet x-ray source, as well as unconventional sources such as a linear accelerator x-ray source, a synchrotron x-ray source, and a Compact Light Source (CLS). In third generation synchrotrons, the x-ray radiation is produced as the electron beam passes through a special magnet called an undulator magnet. The Compact Light Source uses a "laser undulator" to accomplish a similar result. A laser beam colliding with an opposing electron beam may have the same effect as an electron beam passing through an undulator magnet. The electric and magnetic fields of the laser beam cause the electron to wiggle and induce a radiation spectrum similar to that from a long undulator magnet. This radiation is often referred to as Inverse Compton Scattering. If a laser beam with a wavelength of one micron is used, the electron beam energy necessary for 1 Å radiation is only about 25 MeV. This reduces the scale of the CLS device by a factor of about 200 as compared to conventional synchrotron x-ray sources and results in a compact electron storage ring with a footprint comparable to that of a large office desk. In some embodiments, the CLS generates an electron pulse using an RF photocathode and this electron pulse gains energy by passing through accelerator sections. Once a chosen energy is reached, the pulse is injected into the storage ring. The storage ring is designed to allow a bunch to circulate for about one million turns. Periodically, a new pulse is injected to refresh the stored beam in order to maintain a steady, high quality x-ray output beam.

Figure 4B:
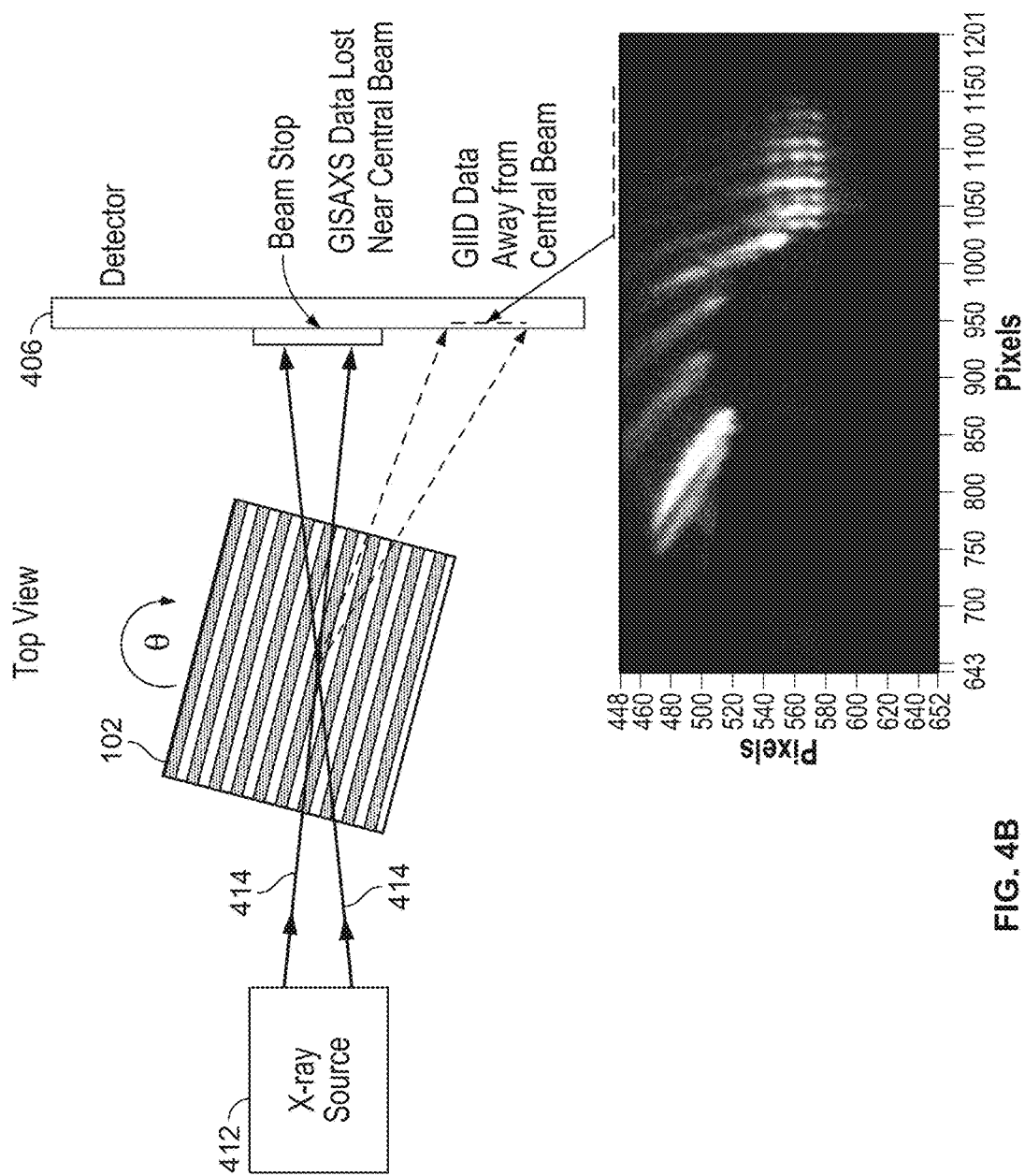
FIG. 4B is a diagram illustrating a top view and FIG. 4C is a diagram illustrating a profile view of an example showing a focused divergent x-ray beam being utilized to capture CD-GIID data in analyzing a manufactured structure.
Figure 4C:
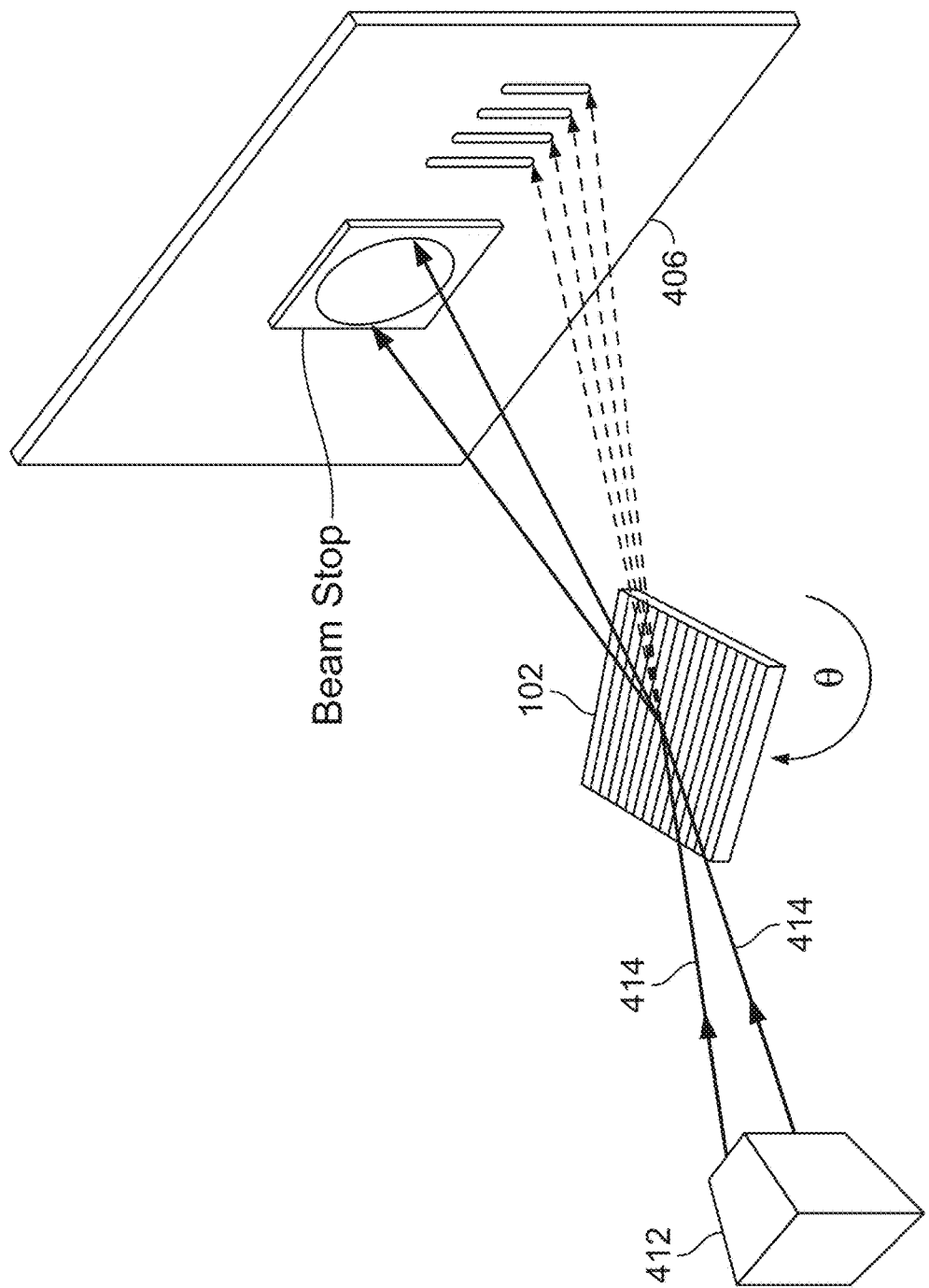

FIG. 4B is a diagram illustrating a top view and FIG. 4C is a diagram illustrating a profile view of an example showing a focused divergent x-ray beam being utilized to capture CD-GIID data in analyzing a manufactured structure. The difference between the example of FIG. 4A and the example of FIGS. 4B/4C is the use of x-ray source 412 outputting a focused beam with a spread of angles in FIGS. 4B/4C. For example, x-ray beam cone 414 typically has a spread of up to 3 milliradians but can be as large as 30 milliradians. Larger angular spread can reveal a greater amount of resonances at the expense of limiting the resolution of low angle resonances due to their overlap with the transmitted (unscattered) beam. It is possible to directly utilize an x-ray beam source with a spread of angles because only the beams that are at particular angles with respect to a surface of the sample will be highly reflected for detection.

The structure of sample 102 effectively acts as an angular filter that has very high reflectivity at only particular angles. Thus, it is possible to directly utilize an x-ray beam source with a divergent spread of angles without utilizing collimation because only the rays that are at particular angles will be highly reflected for detection. The focused beam has more intensity as compared to a beam of same energy that is collimated, thereby decreasing the time necessary for data collection. For example, by allowing more divergence from the x-ray source, more flux is useable for the measurement and can significantly improve throughput. In addition, the spread of angles in the focused beam does not interfere with the measurement (unlike in cases of the CD-SAXS and CD-GISAXS techniques). Also, by using a beam source with a spread of multiple angles, data for multiple beam angles may be collected simultaneously, which effectively reduces the data collection time.

Figure 4D:
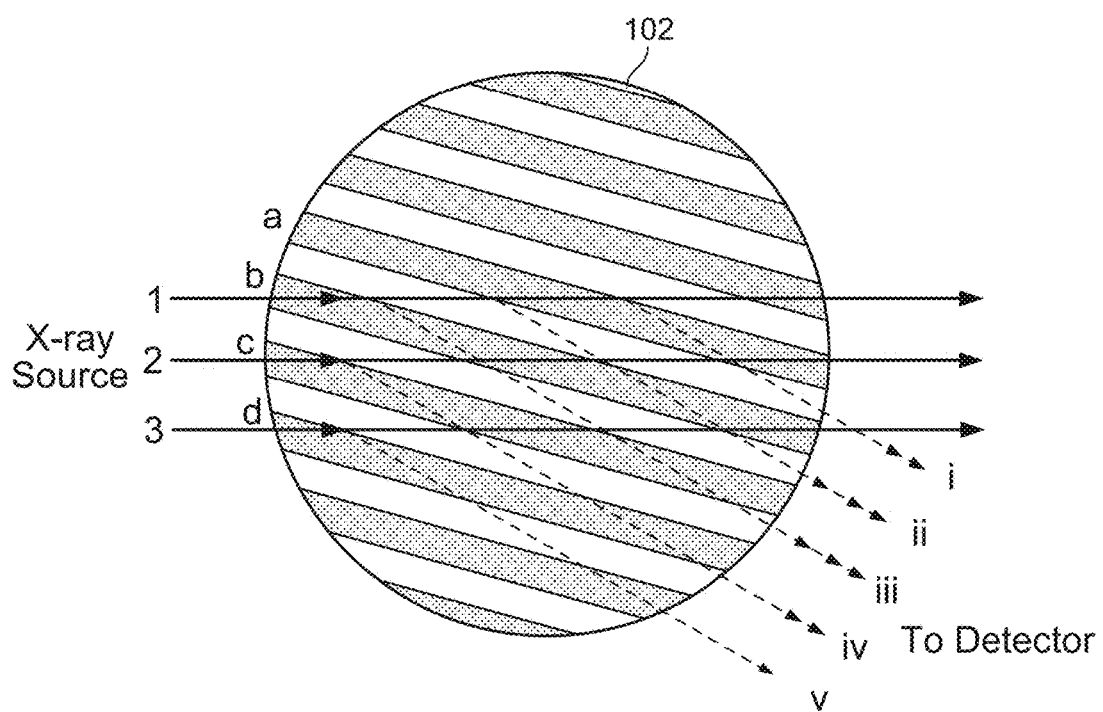
FIG. 4D is a diagram illustrating CD-GIID ray scattering from possible boundaries of features of a sample.

FIG. 4D is a diagram illustrating CD-GIID x-ray scattering from possible boundaries of features of a sample. Several rays can constructively or destructively interfere along their path to produce intensity patterns on a detector. Example x-rays 1, 2, and 3 have multiple opportunities to scatter from boundaries of periodic structures (e.g., rows a-d) of manufactured device sample 102 and be directed toward the detector (positions i-v). For example, the source x-ray 2 may scatter from the interfaces of the structure in rows a, b, and c (in reverse order as it traverses this region) reflecting to possible positions i, ii, iii, and iv. A particular position on the detector has an intensity which is a superposition of rays and depends on both the reflection amplitude and relative phases of all contributing paths. For example, the intensity detected at position ii is a superposition of scattering amplitudes from ray 1→a, 2→b', and 3→b (where b' denotes the back side interface in the beam direction).

Figure 5:
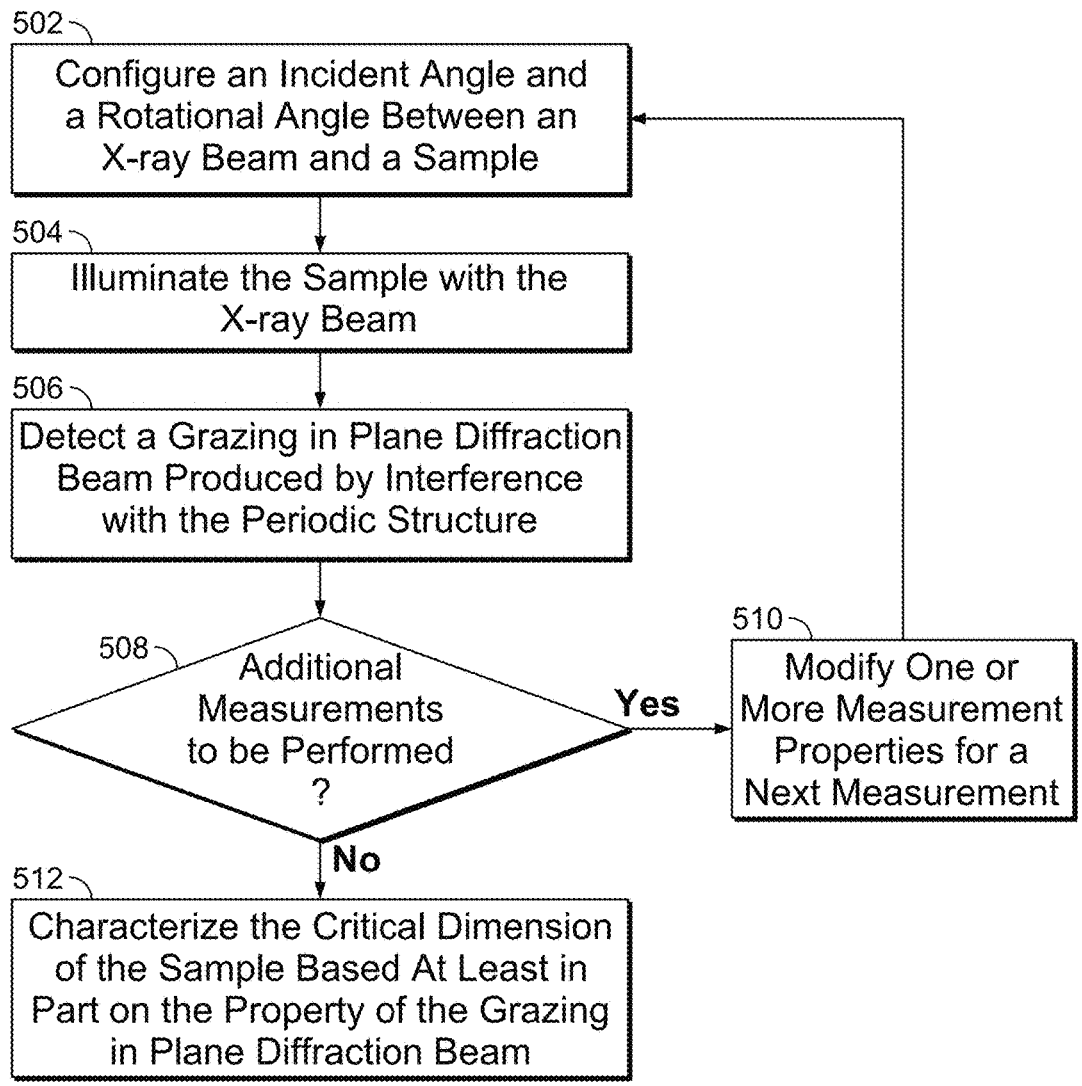
FIG. 5 is a flowchart illustrating an embodiment of a process for processing a grazing in-plane diffraction beam.

FIG. 5 is a flowchart illustrating an embodiment of a process for processing a grazing in-plane diffraction beam. The process of FIG. 5 may be implemented using one or more components shown in FIGS. 4A and/or 4B.

At 502, an incident angle and a rotational angle between an x-ray beam and a sample is configured. Examples of the sample may include a semiconductor device, a nanoscale manufactured device, and any other manufactured device with a periodic feature. The sample may be a part of a semiconductor wafer. In some embodiments, the sample is a test pattern included in a manufactured device. For example, test pads are placed on semiconductor wafers. In some embodiments, multiple pattern techniques are used for the manufacture of devices to increase density of features on nanometer scales. One example is double patterning in which spacers or other masks are used sequentially to create periodic structures that ideally have uniform dimensions. Variations in this process lead to overlay and critical dimensions errors in feature placement and grazing in-plane diffraction beam may be utilized to detect these errors. For fabrication process control, a periodic structure may be deposited uniformly on one or more test pads and is available for in-line measurement during intermediate steps of fabrication. In some embodiments, the sample is a sample being tested off-line from a fabrication process. In some embodiments, the sample includes functional elements of a semiconductor device.

In various embodiments, periodic features of the sample are being tested and the features of the sample are periodic if the features are repeated for at least two periods. However, periodic features are typically repeated for at least ten periods and possibly may be repeated for thousands of periods. In some embodiments, the incident angle is the height angle at which the x-ray beam hits the sample with respect to the plane of the sample. In some embodiments, the incident angle is a grazing angle of the x-ray beam with respect to the normal incidence of the sample. The incident angle is typically less than the critical angle for the material under test, for example approximately 3 milliradians for Silicon at X-ray wavelengths near 1 Å. An example of the incident angle is shown in FIG. 2 as angle $\alpha_i$. In some embodiments, the incident angle has been automatically determined using an analytical model. For example, Kinematic, Parratt, or Kohn's Analytic Formula has been utilized to model multilayer interference effects of the beam on the sample and the ideal incident angle for desired critical dimension characterization is selected. In some embodiments, the incident angle has been determined experimentally.

In some embodiments, the rotation angle is the angle at which a feature of the sample is oriented in the plane of the sample with respect to the beam. In some embodiments, the rotation angle is angle θ shown in FIGS. 4A and 4B. In some embodiments, the rotation angle θ is in the plane perpendicular to the plane of the incident angle. In some embodiments, for a θ angle rotation of the sample with respect to the beam, the beam is reflected 2θ away from the transmitted beam. In some embodiments, by controlling the rotation angle, the x-ray beam can be aligned with respect to the periodic feature of the sample to cause higher order resonant reflections between the features of the sample. For example, for only certain rotation angles between the sample features and the beam, highly defined higher order diffraction patterns can be detected using an in-plane sensor. In some embodiments, the rotation angle has been automatically determined using an analytical model. For example, Kinematic, Parratt, or Kohn's Analytic Formula has been utilized to model multilayer interference effects of the beam on the sample and the ideal rotation angle(s) and incident angle for desired critical dimension characterization are selected. In some embodiments, the rotation angle has been determined experimentally.

In some embodiments, configuring the incident angle and the rotational angle includes positioning/orienting/moving the x-ray beam and/or the sample to satisfy the incident angle and the rotational angle between an x-ray beam and the sample. For example, in certain embodiments, the beam may not be movable and the sample must be oriented in a desired direction/configuration.

At 504, the sample is illuminated with the x-ray beam. In some embodiments, the x-ray beam is a collimated x-ray with substantially parallel rays. In some embodiments, the x-ray beam has not been collimated. In various embodiments, the x-ray beam has been generated using one or more of the following: a microfocus, a rotating anode, a liquid metal jet, a linear accelerator, a synchrotron, and a Compact Light Source (CLS). In some embodiments, illuminating the sample includes focusing an x-ray beam on periodic features of the sample. The surface structure of the sample effectively acts as an angular filter that has very high reflectivity at only particular angles. Thus, it is possible to directly utilize an x-ray beam source with a spread of angles without collimation because only the beams that are at particular angles will be highly reflected for detection. In some embodiments, the spot size of the x-ray beam has been determined based on the dimension of a geometric cross-section of the sample to be measured.

At 506, a grazing in-plane diffraction beam produced by interference with the periodic structure is detected. For example, when the x-ray beam hits the periodic structure of the sample, the beam is reflected and higher order reflections from periodic structural elements are created. At certain angles, these higher order reflections have phase shifts between the reflected beams that constructively and destructively interfere to cause variations on diffraction pattern properties detected on a detector that can be analyzed to determine properties of the critical dimensions of the sample. One or more properties of the grazing in-plane diffraction beam are determined by the critical dimension. For example, the properties include the intensity, angle, and/or position (e.g., x and y location coordinates) of a diffraction pattern on the detector.

At 508, it is determined whether additional measurements are to be performed. For example, one or more measurement properties are to be modified between measurements to iteratively build a combined data for analysis. Multiple measurement scans may be performed by changing the rotation angle of the sample with respect to the beam for each measurement instance and the results of multiple measurements (e.g., multiple diffraction patterns) may be combined together to create a combined diffraction pattern with many orders of reflections in the plane of an area of the detector. This combined diffraction pattern may be analyzed to characterize the critical dimensions of the sample. In some embodiments, a range of angles greater than those contained in the spread of the beam is achieved by rotating the beam source, or the sample, in-plane (rotation angle) and tracking the overall reflections onto the detector. A diffraction image is acquired at each static step, with suitable overlap from one image to the next for each measurement is collected and a full data set for analysis is generated by registering and combining images. In some embodiments, three-dimensional data of the sample may be captured by rotating the sample 90 degrees and repeating the measurement process.

If at 508 it is determined that additional measurements are to be performed, at 510 one or more measurement properties are modified for a next measurement and the process returns to 502. In various embodiments, one or more of the following measurement properties are adjusted: the rotation angle, the incident angle, a beam intensity, a detector setting, etc.

If at 508 it is determined that additional measurements are not to be performed, at 512, the critical dimension of the sample is characterized based at least in part on the property of the grazing in-plane diffraction beam. In some embodiments, characterization of the critical dimension of the sample is associated with statistical measurements that are sensitive to cross section dimensions related to thickness, height, layer, gap, width, angle, undercut, type of material, shape, and roughness of interfaces in a periodic structure. Examples of the critical dimension include sidewall angle, line height, linewidth, pitch, undercut, amplitude of linewidth roughness and line-edge roughness, etc. In some embodiments, due to the non-destructive nature of x-ray measurements, the critical dimension characterization is a part of an inline semiconductor fabrication process (e.g., to detect deviation of the manufactured structure from the nominal structure) and/or an offline testing process. In some embodiments, based on the critical dimension characterization, one or more measurements of the periodic features of the sample are determined. In some embodiments, based on the critical dimension characterization, a measure of deviation from a reference ideal is determined. For example, if the measure of deviation is outside a tolerance range, the sample is identified as defective. In some embodiments, characterizing the critical dimension includes generating a representational two-dimensional model and/or three-dimensional model of the periodic feature and/or the critical dimension.

Figure 6:
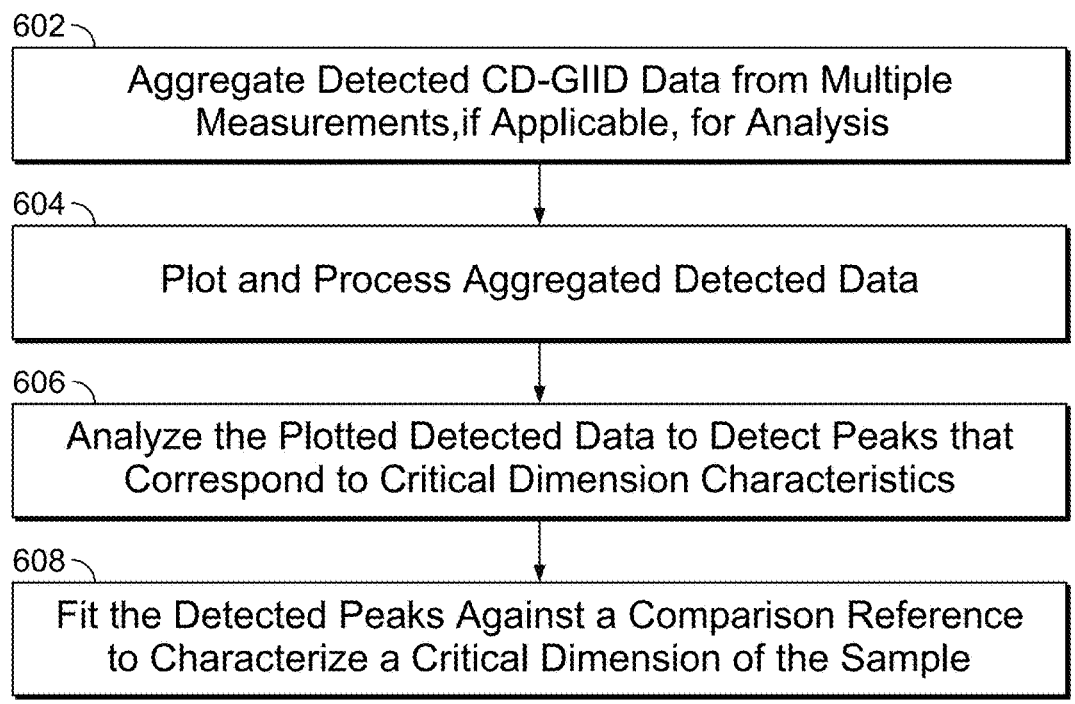
FIG. 6 is a flowchart illustrating an embodiment of a process for characterizing a critical dimension.

FIG. 6 is a flowchart illustrating an embodiment of a process for characterizing a critical dimension. The process of FIG. 6 may be implemented using one or more components shown in FIGS. 4A, 4B and/or 4C. In some embodiments, one or more steps of the process of FIG. 6 are included in 512 of FIG. 5.

Figure 7A:
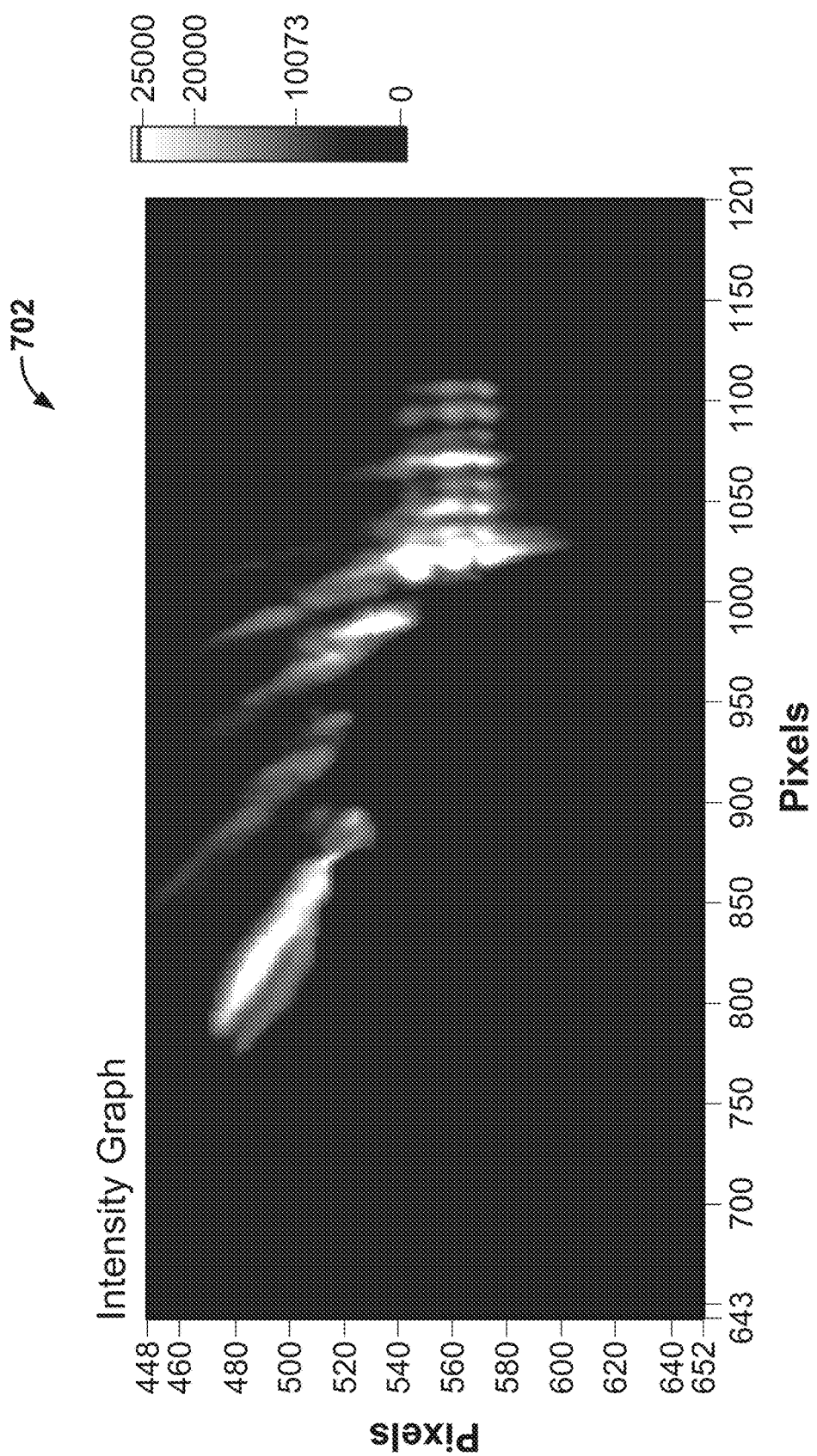
FIG. 7A shows intensity pattern 702 of detected data at a given in-plane rotation angle.

At 602, detected CD-GIID data from multiple measurements is aggregated, if applicable, for analysis. For example, data collected in each iteration of the process of FIG. 5 is combined together. For example, FIG. 7A shows intensity pattern 702 of detected data at a given in-plane rotation angle (e.g., angle θ). Due to a focused x-ray beam containing a spread of angles, graph 702 reveals several orders of reflections determined by interference conditions at particular angles included in the incident beam. The grazing reflected angle (e.g., angle $\alpha_f$) is represented as a vertical axis in the pattern. FIG. 7B shows intensity pattern 704 that depicts an aggregation of several intensity patterns at different in-plane rotation angles in log scale. Pattern 702 is one of many other patterns aggregated to form pattern 704. A large set of reflection orders is shown in pattern 704. The center vertical line defines the aligned case (θ=0), where the overall structure is parallel with the beam. The top and bottom horizontal lines form a box in which the in-plane data is projected. By combining patterns from the in-plane rotation scan (θ), a normalized series of intensity peaks appear, separated in even intervals in the in-plane (θ) direction, and as streaks in the out-of-plane ($\alpha_f$) direction that contain out-of-plane information (e.g., heights and sidewall slopes). In addition, reflections are induced with $\alpha_f$ substantially different from $\alpha_i$, which can be seen in FIG. 7B. These non-specular reflections are due to the 3D Bragg/Laue equation and may also be analyzed with methods similar to those discussed above.

Figure 7C:
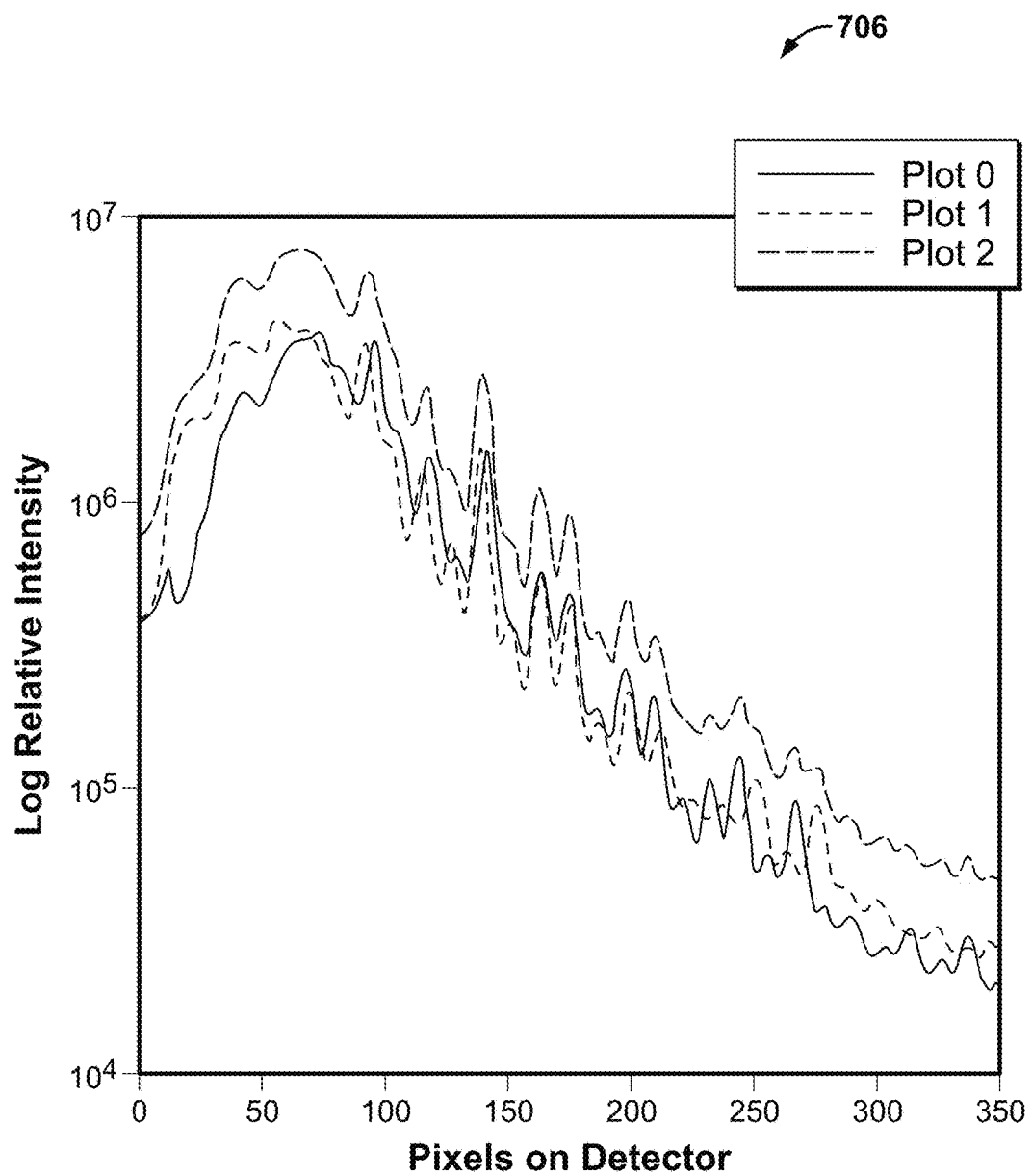
FIG. 7C shows plot 706 of a projection of pattern 704 along the horizontal axis showing relative intensity peaks.

Returning to FIG. 6, at 604, aggregated detected data is plotted and processed. For example, by combining intensity patterns from the in-plane rotation scan (θ), a normalized series of intensity peaks appear, separated in even intervals in the in-plane (θ) direction, and as streaks in the out-of-plane ($\alpha_f$) direction that contain out-of-plane information. To determine the average (in-plane) spacing parameters, the streaks can be projected onto the in-plane axis and plotted as a function of θ. The intensity distribution has a broad characteristic background with periodic peaks of various relative intensities spaced at the super-period of the sample (and calibrated after converting angles to q-space). For example, FIG. 7C shows plot 706 of a projection of pattern 704 along the horizontal axis showing relative intensity peaks on top of a scattering profile. Pattern 704 has been divided and folded along θ=0 and projected to produce plot 706. Plot 0 plots data on the right side of the center line of pattern 704 and plot 1 plots data on the left side of the center line of pattern 704. As expected, the right side plot and the left side plot are nearly identical due to the same periodic structure producing nearly same diffraction pattern on each side as the sample is rotated along θ. Plot 2 plots the sum of plot 0 and plot 1.

Figure 7D:
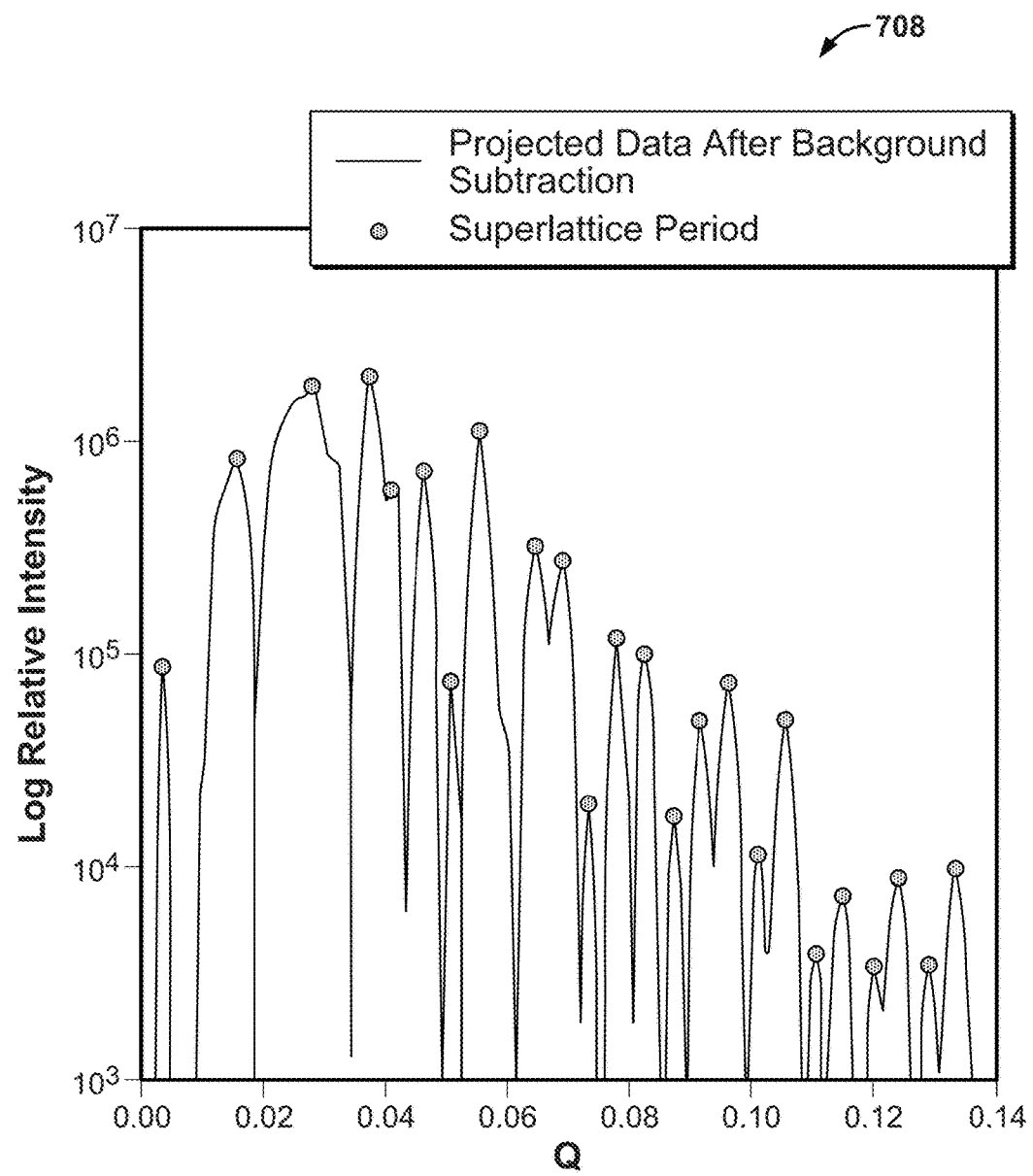
FIG. 7D shows plot 708 resulting after plot 706 has been smoothed using a smoothing function to remove background baseline (e.g., due to the substrate of the sample) and the periodic peaks can be fit with uniform spacing in Q space determined by a super-period of the pattern.

Returning to FIG. 6, at 606, the plotted detected data is analyzed to detect peaks that correspond to critical dimension characteristics. For example, FIG. 7D shows plot 708 resulting after plot 706 has been smoothed using a smoothing function to remove background baseline (e.g., due to the substrate of the sample) and the periodic peaks can be fit with uniform spacing in Q space determined by a super-period of the pattern. The resulting points shown in plot 708 include information about the relative weighting of each reflection order.

Figure 7E:
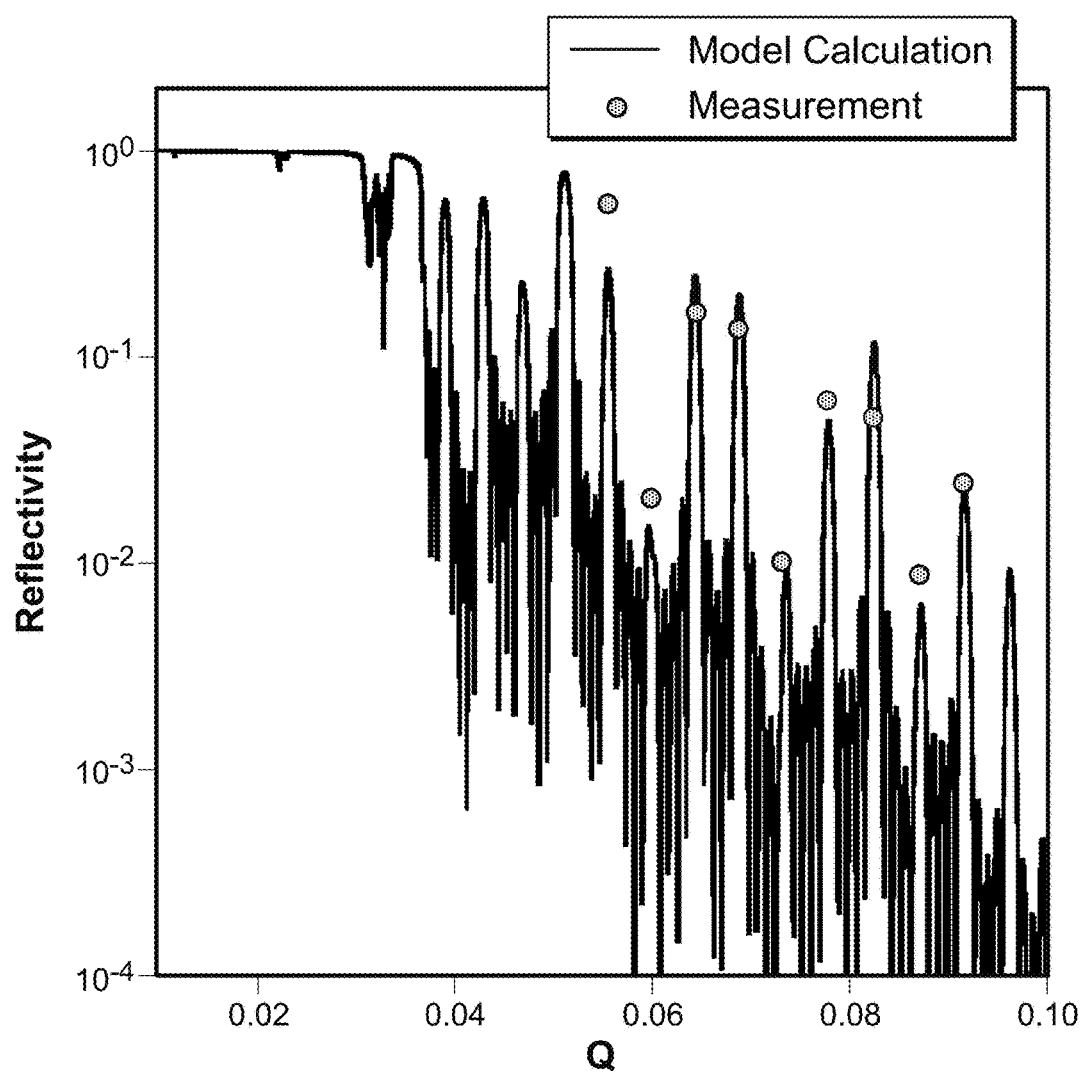
FIG. 7E shows plot 710 of a reference model of an ideal nominal structure.
Figure 7F:
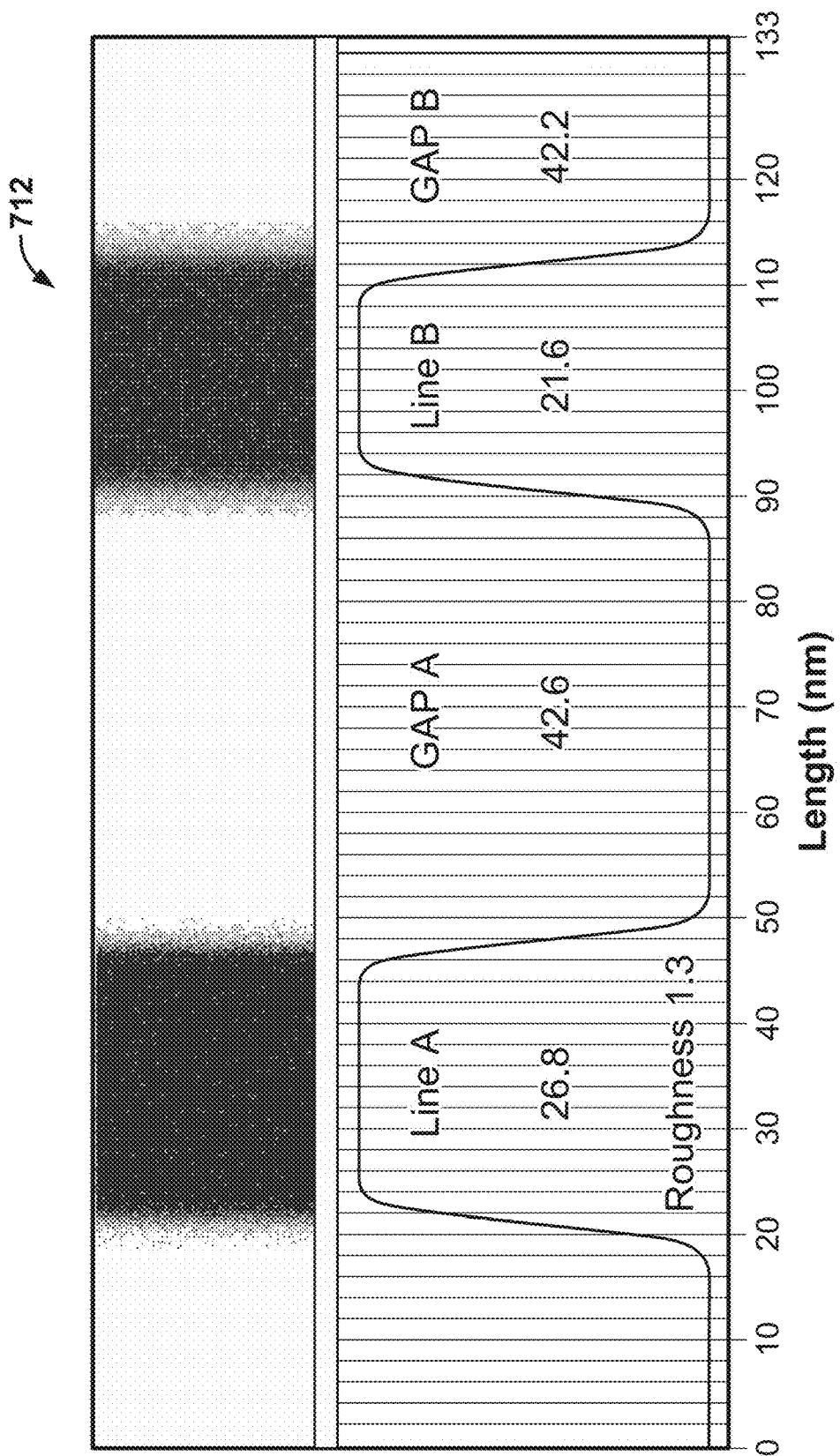
FIG. 7F shows graphical representation 712 of the reference model calculated in FIG. 7E illustrating detected critical dimension characteristics.

Returning to FIG. 6, at 608, the detected peaks are fit against a comparison reference to characterize a critical dimension of the sample. For example, FIG. 7E shows plot 710 of a reference model of an ideal nominal structure. The subset of the peak points shown in plot 708 are shown on plot 710. FIG. 7F shows graphical representation 712 graphically illustrating the detected critical dimension characteristics parameterized by the peak points shown in plot 710 of FIG. 7E. Ideally the two line widths and gap spaces would be identical in representation 712.

Returning to FIG. 6, the data of the detected CD-GIID beam is compared against reference data of an expected GIID beam (e.g., expected GIID beam produced by an ideal nominal sample). In some embodiments, the comparison reference and/or data of the expected GIID beam may be generated using an analytical simulation model of an ideal nominal sample. For example, one or more of the following analytical models are utilized to generate the reference: Kinematic, Parratt, Kohn's Analytic Formula, Parratt Recursion Formula, and generalized Weighted Superposition Approximation. In some embodiments, the relative intensity weighting of the peaks is highly sensitive to the parameters of the periodic structure and can be fit to models. These models may be generated by analytic methods or through generalized electrodynamic modeling, for example using finite element matrix methods. Since there are typically many orders of resonance along the in-plane direction (θ), the relative weights of many data points can be least-square fit to a finite collection of parameters. In some embodiments, the reference may be generated by measuring a known good sample to experimentally generate a reference dataset. For example, the known good sample is measured using the process of FIG. 5 and measurement results are stored as the comparison reference. In some embodiments, characterizing the critical dimension includes comparing the detected data with the comparison reference and determining a measure of deviation. For example, if the measure of deviation is outside a tolerance range, the sample is identified as defective. In some embodiments, characterizing the critical dimension includes generating a representational two-dimensional and/or three-dimensional model of the periodic structure and/or the critical dimension. In some embodiments, characterizing the critical dimension includes determining a critical dimension measurement value by determining which comparison reference of a plurality of references is the closest match to the detected data, and a measurement data corresponding to the closest match is selected as the critical dimension measurement value. If more than one match has been identified, measurement data of the matches may be averaged or otherwise statistically processed to determine the measurement value corresponding to the detected data.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for analyzing a manufactured structure having a periodic feature characterized by a critical dimension including:
    a x-ray beam source configured to illuminate the manufactured structure with an x-ray beam, wherein the manufactured structure is positioned at a selected grazing angle and a selected rotation angle with respect to the x-ray beam and the selected rotation angle has been selected to enhance in-plane diffraction of reflections of the x-ray beam by the manufactured structure;
    a detector configured to detect a grazing in-plane diffraction beam produced by interference with the periodic feature, wherein a property of the grazing in-plane diffraction beam is determined by the critical dimension; and
    a processor configured to characterize the critical dimension based on the property of the grazing in-plane diffraction beam.

2. The system of claim 1, wherein the system is utilized inline in a semiconductor manufacturing process to detect deviation of the manufactured structure from a reference.

3. The system of claim 1, wherein the manufactured structure is at least a portion of a semiconductor device.

4. The system of claim 1, wherein the x-ray beam illuminating the manufactured structure has been collimated.

5. The system of claim 1, wherein the x-ray beam illuminating the manufactured structure has not been collimated.

6. The system of claim 1, wherein divergent rays of the x-ray beam illuminating the manufactured structure have been focused on the manufactured structure.

7. The system of claim 1, wherein the x-ray beam illuminating the manufactured structure has a divergence greater than 3 milliradians.

8. The system of claim 1, wherein characterizing the critical dimension includes determining a measurement value of structure parameters of the critical dimension.

9. The system of claim 1, wherein characterizing the critical dimension includes comparing the property of the grazing in-plane diffraction beam with a model generated property of an expected grazing in-plane diffraction beam.

10. The system of claim 9, wherein the model generated property of the expected grazing in-plane diffraction beam was generated using a Parratt analytical model.

11. The system of claim 1, wherein the selected rotation angle includes an in-plane rotation angle in a plane of the manufactured structure and the in-plane rotation angle has been selected to enhance a diffraction pattern produced by the grazing in-plane diffraction beam when in-plane reflected x-ray paths are superposed.

12. The system of claim 1, wherein the detector is a two-dimensional detector including scintillator-coupled CCDs.

13. The system of claim 1, wherein detecting the grazing in-plane diffraction beam includes detecting a diffraction pattern caused at least in part by multiple reflections of a single ray on multiple surfaces of the periodic feature.

14. The system of claim 1, wherein detecting the grazing in-plane diffraction beam includes detecting a Laue-Bragg diffraction.

15. The system of claim 1, wherein the property of the grazing in-plane diffraction beam includes one or more of the following: an intensity, an angle, and a position.

16. The system of claim 1, wherein the critical dimension includes one or more of the following: a sidewall angle, a line height, a linewidth, a pitch, and a roughness.

17. The system of claim 1, wherein characterizing the critical dimension includes aggregating properties of grazing in-plane diffraction beams detected at different measurement instances corresponding to different rotation angles.

18. The system of claim 1, wherein characterizing the critical dimension includes detecting one or more peaks of a plot of the property of the grazing in-plane diffraction beam.

19. A method for analyzing a manufactured structure having a periodic feature characterized by a critical dimension including:
illuminating the manufactured structure with an x-ray beam, wherein the manufactured structure is positioned at a selected grazing angle and a selected rotation angle with respect to the x-ray beam and the selected rotation angle has been selected to enhance in-plane diffraction of reflections of the x-ray beam by the manufactured structure;
detecting a grazing in-plane diffraction beam produced by interference with the periodic feature, wherein a property of the grazing in-plane diffraction beam is determined by the critical dimension; and
characterizing the critical dimension based on the property of the grazing in-plane diffraction beam.

20. The method of claim 19, wherein characterizing the critical dimension includes detecting a deviation of the manufactured structure from a reference as a part of a semiconductor manufacturing process.

21. The method of claim 19, wherein the manufactured structure is at least a portion of a semiconductor device.

22. The method of claim 19, wherein the x-ray beam illuminating the manufactured structure has been collimated.

23. The method of claim 19, wherein the x-ray beam illuminating the manufactured structure has not been collimated.

24. The method of claim 19, wherein divergent rays of the x-ray beam illuminating the manufactured structure have been focused on the manufactured structure.

25. The method of claim 19, wherein the x-ray beam illuminating the manufactured structure has a divergence greater than 3 milliradians.

26. The method of claim 19, wherein characterizing the critical dimension includes determining a measurement value of structure parameters of the critical dimension.

27. The method of claim 19, wherein characterizing the critical dimension includes comparing the property of the grazing in-plane diffraction beam with a model generated property of an expected grazing in-plane diffraction beam.

28. The method of claim 27, wherein the model generated property of the expected grazing in-plane diffraction beam was generated using a Parratt analytical model.

29. The method of claim 19, wherein the selected rotation angle includes an in-plane rotation angle in a plane of the manufactured structure and the in-plane rotation angle has been selected to enhance a diffraction pattern produced by the grazing in-plane diffraction beam when in-plane reflected x-ray paths are superposed.

30. The method of claim 19, wherein the grazing in-plane diffraction beam is detected using a two-dimensional detector including scintillator-coupled CCDs.

31. The method of claim 19, wherein detecting the grazing in-plane diffraction beam includes detecting a diffraction pattern caused at least in part by multiple reflections of a single ray on multiple surfaces of the periodic feature.

32. The method of claim 19, wherein detecting the grazing in-plane diffraction beam includes detecting a Laue-Bragg diffraction.

33. The method of claim 19, wherein the property of the grazing in-plane diffraction beam includes one or more of the following: an intensity, an angle, and a position.

34. The method of claim 19, wherein the critical dimension includes one or more of the following: a sidewall angle, a line height, a linewidth, a pitch, and a roughness.

35. The method of claim 19, wherein characterizing the critical dimension includes aggregating properties of grazing in-plane diffraction beams detected at different measurement instances corresponding to different rotation angles.

36. The method of claim 19, wherein characterizing the critical dimension includes detecting one or more peaks of a plot of the property of the grazing in-plane diffraction beam.

37. A computer program product for analyzing a manufactured structure having a periodic feature characterized by a critical dimension, the computer program product being embodied in a tangible computer readable storage medium and comprising computer instructions for:

illuminating the manufactured structure with an x-ray beam, wherein the manufactured structure is positioned at a selected grazing angle and a selected rotation angle with respect to the x-ray beam and the selected rotation angle has been selected to enhance in-plane diffraction of reflections of the x-ray beam by the manufactured structure;

detecting a grazing in-plane diffraction beam produced by interference with the periodic feature, wherein a property of the grazing in-plane diffraction beam is determined by the critical dimension; and characterizing the critical dimension based on the property of the grazing in-plane diffraction beam.

38. The computer program product of claim 37, wherein characterizing the critical dimension includes detecting a deviation of the manufactured structure from a reference as a part of a semiconductor manufacturing process.

39. The computer program product of claim 37, wherein the manufactured structure is at least a portion of a semiconductor device.

40. computer program product of claim 37, wherein the x-ray beam illuminating the manufactured structure has been collimated.

41. The computer program product of claim 37, wherein the x-ray beam illuminating the manufactured structure has not been collimated.

42. The computer program product of claim 37, wherein divergent rays of the x-ray beam illuminating the manufactured structure have been focused on the manufactured structure.

43. The computer program product of claim 37, wherein the x-ray beam illuminating the manufactured structure has a divergence greater than 3 milliradians.

44. The computer program product of claim 37, wherein characterizing the critical dimension includes determining a measurement value of structure parameters of the critical dimension.

45. The computer program product of claim 37, wherein characterizing the critical dimension includes comparing the property of the grazing in-plane diffraction beam with a model generated property of an expected grazing in-plane diffraction beam.

46. The computer program product of claim 45, wherein the model generated property of the expected grazing in-plane diffraction beam was generated using a Parratt analytical model.

47. The computer program product of claim 37, wherein the selected rotation angle includes an in-plane rotation angle in a plane of the manufactured structure and the in-plane rotation angle has been selected to enhance a diffraction pattern produced by the grazing in-plane diffraction beam when in-plane reflected x-ray paths are superposed.

48. The computer program product of claim 37, wherein the grazing in-plane diffraction beam is detected using a two-dimensional detector including scintillator-coupled CCDs.

49. The computer program product of claim 37, wherein detecting the grazing in-plane diffraction beam includes detecting a diffraction pattern caused at least in part by multiple reflections of a single ray on multiple surfaces of the periodic feature.

50. The computer program product of claim 37, wherein detecting the grazing in-plane diffraction beam includes detecting a Laue-Bragg diffraction.

51. The computer program product of claim 37, wherein the property of the grazing in-plane diffraction beam includes one or more of the following: an intensity, an angle, and a position.

52. The computer program product of claim 37, wherein the critical dimension includes one or more of the following: a sidewall angle, a line height, a linewidth, a pitch, and a roughness.

53. The computer program product of claim 37, wherein characterizing the critical dimension includes aggregating properties of grazing in-plane diffraction beams detected at different measurement instances corresponding to different rotation angles.

54. The computer program product of claim 37, wherein characterizing the critical dimension includes detecting one or more peaks of a plot of the property of the grazing in-plane diffraction beam.

\* \* \* \* \*